US008264265B2

(12) United States Patent
Greiner et al.

(10) Patent No.: US 8,264,265 B2
(45) Date of Patent: Sep. 11, 2012

(54) AUTOMATIC DARKENING FILTER (ADF) EYE PROTECTION DEVICE WITH IMPROVED DRIVE CIRCUITRY

(75) Inventors: Donald William Greiner, Grandville, MI (US); Thomas Joe Hamilton, Holland, MI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 7 days.

(21) Appl. No.: 12/894,739

(22) Filed: Sep. 30, 2010

(65) Prior Publication Data

US 2012/0081162 A1    Apr. 5, 2012

(51) Int. Cl.
*A61F 9/06* (2006.01)
*G02B 5/30* (2006.01)
*G02F 1/1335* (2006.01)

(52) U.S. Cl. .............. 327/268; 327/290; 2/431; 349/14; 349/104; 359/601

(58) Field of Classification Search .................. None
See application file for complete search history.

(56) References Cited

U.S. PATENT DOCUMENTS

| | | | |
|---|---|---|---|
| 4,491,390 A | 1/1985 | Tong-Shen | |
| 5,533,206 A | 7/1996 | Petrie et al. | |
| 6,643,146 B2 * | 11/2003 | Boeke | 363/17 |
| 6,750,842 B2 * | 6/2004 | Yu | 345/102 |
| 7,446,292 B2 * | 11/2008 | Hamilton | 250/201.1 |
| 7,477,330 B2 | 1/2009 | Magnusson et al. | |
| 7,637,622 B2 | 12/2009 | Garbergs et al. | |
| 2004/0178326 A1 | 9/2004 | Hamilton et al. | |

FOREIGN PATENT DOCUMENTS

| | | |
|---|---|---|
| EP | 1 190 689 A2 | 3/2002 |
| WO | WO 93/13397 | 7/1993 |
| WO | WO 00/54097 | 9/2000 |
| WO | WO 00/62119 | 10/2000 |

OTHER PUBLICATIONS

PCT Search Report, Dec. 1, 2011.

\* cited by examiner

*Primary Examiner* — Lincoln Donovan
*Assistant Examiner* — Terry L Englund
(74) *Attorney, Agent, or Firm* — Dority & Manning, P.A.

(57) ABSTRACT

An apparatus and methodology for operating an automatic darkening filter (ADF) eye protection device alternately applies an operating voltage to a pair of control terminals of an ADF device circuit in a continuing sequence, where a first polarity voltage is applied to the pair of terminals and then reversed. A delay period is provided between application of the alternating polarities. In some embodiments ground potential is applied to both terminals of the pair of terminals during the delay period.

9 Claims, 2 Drawing Sheets

AUTOMATIC DARKENING FILTER (ADF) EYE PROTECTION DEVICE WITH IMPROVED DRIVE CIRCUITRY

FIELD OF THE INVENTION

The present subject matter relates generally to automatic darkening filter (ADF) eye protection devices, and more particularly to ADF devices having an improved drive circuit.

BACKGROUND OF THE INVENTION

Automatic darkening filter (ADF) eye protection devices are employed in a number of fields. One such field is welding where ADF technology provides protection for welders' eyes from the intense light levels generated in the welding process. Eye protection devices may also be used in other areas where bright light may be generated such as from lasers, explosives, etc.

ADF systems often include a liquid crystal device (LCD) that is generally driven with shade voltages applied across the filter corresponding to an alternating current (AC) square wave, To provide this square wave voltage, the voltage polarity across the filter is constantly being reversed. According to current technology, when the polarity of the voltage across the filter is switched from positive to negative or negative to positive, it is switched very close to instantaneously. Such near instantaneous switching causes high peak currents that stress electronic components and produce high battery drain.

In view of these known disadvantages, it would be advantageous to provide a mechanism for ADF circuitry that eliminates, or at least significantly reduces, the previously experienced high battery drain and component stress.

SUMMARY OF THE INVENTION

Aspects and advantages of the invention will be set forth in part in the following description, or may be obvious from the description, or may be learned through practice of the invention.

In view of the recognized disadvantages encountered in the prior art and addressed by the present subject matter, an improved circuit is provided for operating an automatic darkening filter (ADF) comprising a liquid crystal device (LCD) filter having first and second control terminals to which are coupled first through fourth driver circuits. First through fourth time delay circuits are associated with each of the first through fourth driver circuits. The timer circuits, under control of a switch control circuit, operate to delay application of control voltages to the LCD filter control terminals so that the polarity of an applied control voltage is sequentially reversed periodically based on the time delay produced by the time delay circuits and the operating frequency of a signal applied to a switch control circuit.

In certain embodiments, a ground reference voltage is applied to both control terminals of the liquid crystal device (LCD) filter during the delay periods produced by the time delay circuits.

In accordance with further aspects of the present subject matter, methodologies have been developed for operating an automatic darkening filter (ADF) circuit comprising alternately reversing the polarity of a voltage supply applied to a pair of control terminals for the ADF circuit. In certain embodiments, the method provides for delaying application of the voltage supply in a first polarity for a predetermined time following removal of the voltage applied at a second polarity.

In some embodiments, the method also provides for delaying application of the voltage supply to the pair of control terminals at a second polarity for a predetermined time following removal of the supply applied at the first polarity. In certain other embodiments, the predetermined time is determined based on the time required to charge a capacitor through a resistor to a predetermined voltage level. In still further embodiments, a reference potential is applied to both control terminals during the predetermined time.

Additional objects and advantages of the present subject matter are set forth in, or will be apparent to, those of ordinary skill in the art from the following detailed description and appended claims. The accompanying drawings, which are incorporated in and constitute a part of this specification, illustrate embodiments of the invention and, together with the description, serve to explain the principles of the invention

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

Figures 1, 2:
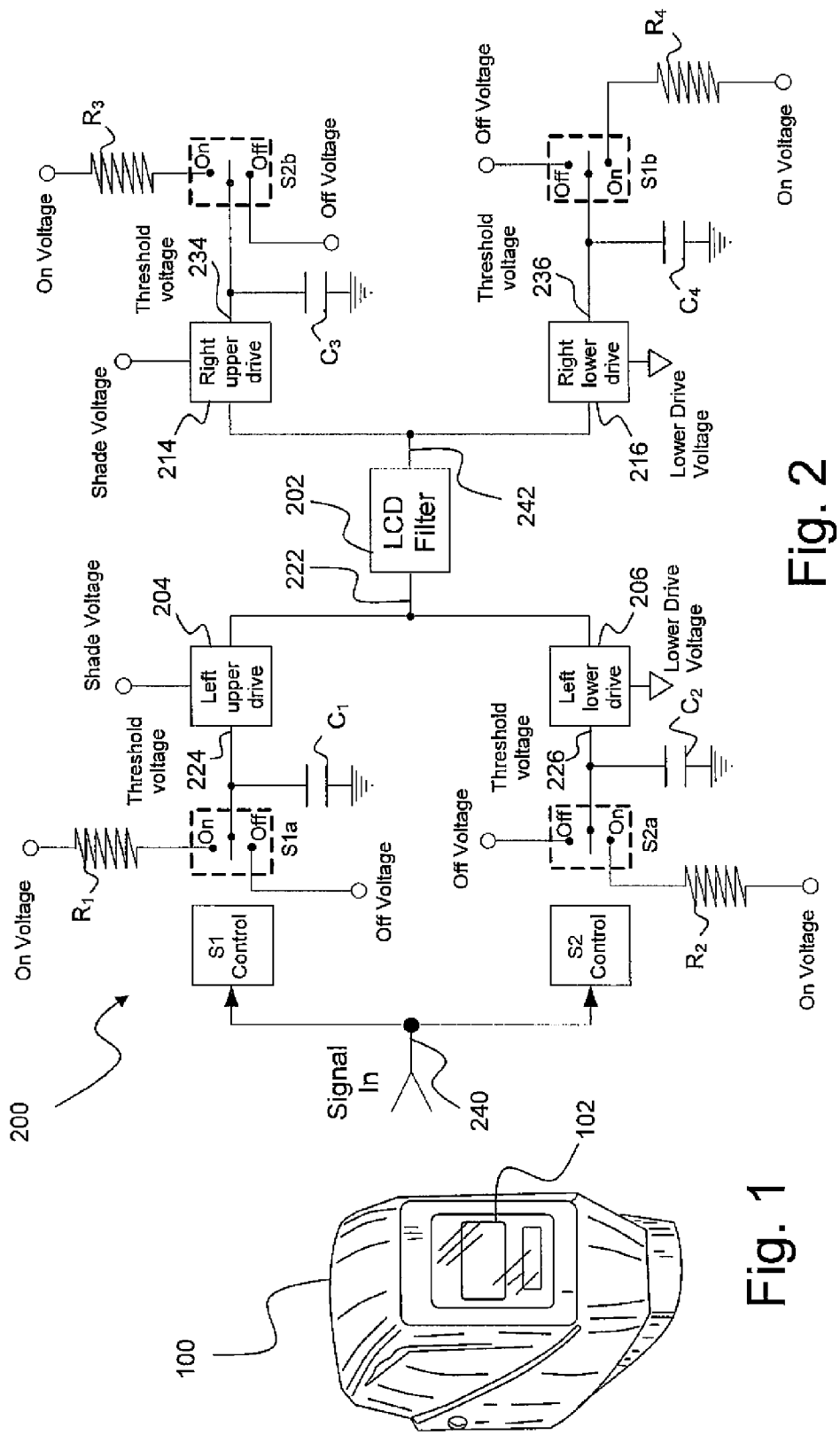
FIG. 1 is a perspective view of an ADF weld helmet that may utilize the improved driver circuitry according to aspects of the present invention.
FIG. 2 is a schematic block diagram of a circuit for use as an automatic darkening filter driver circuit in accordance with present technology.

Repeat use of reference characters throughout the present specification and appended drawings is intended to represent same or analogous features or elements of the invention.

DETAILED DESCRIPTION OF THE PREFERRED EMBODIMENTS

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention include such modifications and variations as come within the scope of the appended claims and their equivalents.

As discussed in the Summary of the Invention section, the present subject matter is particularly concerned with automatic darkening filter (ADF) devices and systems having improved driver circuits. The present invention is not limited to any particular type of ADF system or device. As mentioned, a well-known use of ADF systems is in weld helmets and, in this regard, an ADF weld helmet 100 is depicted in FIG. 1 for illustrative purposes only. The weld helmet 100 includes, among other features, an LCD lens 102 on its front side or face. LCD lens 102 is positioned directly in front of the eyes of the wearer, thereby functioning as the viewing window.

Referring now to FIG. 2, there is illustrated a schematic block diagram of a circuit 200 for use as an ADF driver circuit usable with weld helmet 100 in accordance with aspects of the invention. As is understood by those of ordinary skill in the art, ADF devices generally include a liquid crystal device (LCD) filter 202 that is configured to be placed between a user's eyes and an intense light source for protection of the user's eyes. LCD filter 202 is configured to be pulsed by four drivers corresponding to left upper driver 204, left lower driver 206, right upper driver 214, and right lower driver 216 by application of alternating polarity pulses across terminals 222, 242 of LCD filter 202. Drivers 204, 206, 214, 216 are turned on and off in pairs to form an H-bridge. In such a configuration, left upper driver 204 and right lower driver 216 are on at the same time while left lower driver 206 and right upper driver 214 are off. In alternating fashion, right upper driver 214 and left lower driver 206 are on at the same time while right lower driver 216 and left upper driver 204 are off.

Each driver includes a control pin 224, 226, 234, 236 configured to receive a control voltage that, if of sufficient magnitude, that is, if above a predetermined threshold voltage level, will turn the driver on; otherwise the driver will be turned off. The predetermined threshold level may be established by a comparator or threshold circuit that is a part of the driver circuit.

The four drivers 204, 206, 214, 216 are controlled by two control switches S1 and S2. Switch S1 is configured to control the left upper driver 204 and right lower driver 216 as schematically illustrated by designations S1*a* and S*ib*, respectively. Switch S2 is configured to control the lower left driver 206 and upper right driver 214 as schematically illustrated by designations S2*a* and S2*b*, respectively.

In operation, an electrical input signal is applied to Signal In line 240 to provide control signals to both control switches S1 and S2. The signal applied to line 240 may correspond to a square wave with amplitudes corresponding to logic high and logic low voltages. Switches S1 and S2 are configured such that during logic high, S1 is on and S2 is off while during logic low, S1 is off and S2 is on.

In accordance with the present technology, a delay component has been added so as to delay the operations of the switch S1*a*, S*ib*, S2*a* and S2*b*. The delay insures that there is no overlap of conduction states between the left and right side drivers that would result in a momentary shunting of the Shade Voltage supply to the lower drive voltage which may be at ground potential or anther suitable voltage level, accompanied by a resultant spike in current drawn from the Shade Voltage supply. The Shade Voltage supply, along with other operating voltages including the On Voltage and Off Voltage may be derived from an unillustrated relatively low voltage battery power supply.

As may be seen from a further inspection of FIG. 2, each drive circuit includes a series connected resistor and capacitor, generally indicated as $R_n$ and $C_n$ (where n ranges from 1 to 4), at whose junction a ramp voltage is produced depending on the values of the resistor and capacitor and the applied voltages. Thus, for example, resistor $R_1$ and capacitor $C_1$ are included in the input circuit to left upper driver 204. Resistor $R_1$ is connected at one end to control pin 224 of left upper driver 204 and at the other end to an On Voltage power source. Capacitor $C_1$ is connected at one end to control pin 224 and at the other end to a ground potential connection point.

In similar fashion, resistor-capacitor series pairs $R_2, C_2$ are coupled between an On Voltage supply and ground and at their junction to control pin 226; $R_3, C_3$ are coupled between an On Voltage supply and ground and at their junction to control pin 234; and $R_4, C_4$ are coupled between an On Voltage supply and ground and at their junction to control pin 236.

Each of the switches S1*a*, S1*b*, S2*a*, and S2*b* includes an off terminal coupled to an Off Voltage source. In an exemplary configuration, the Off Voltage source may correspond to a ground potential, although any other voltage level less than threshold levels 306, 314 (FIG. 3) may be used. One purpose of the Off Voltage level is to reset the timing function provided by the series resistor-capacitor circuit, thus the choice of a relatively zero voltage, that is ground potential, would be convenient, but not specifically required.

Figure 3:
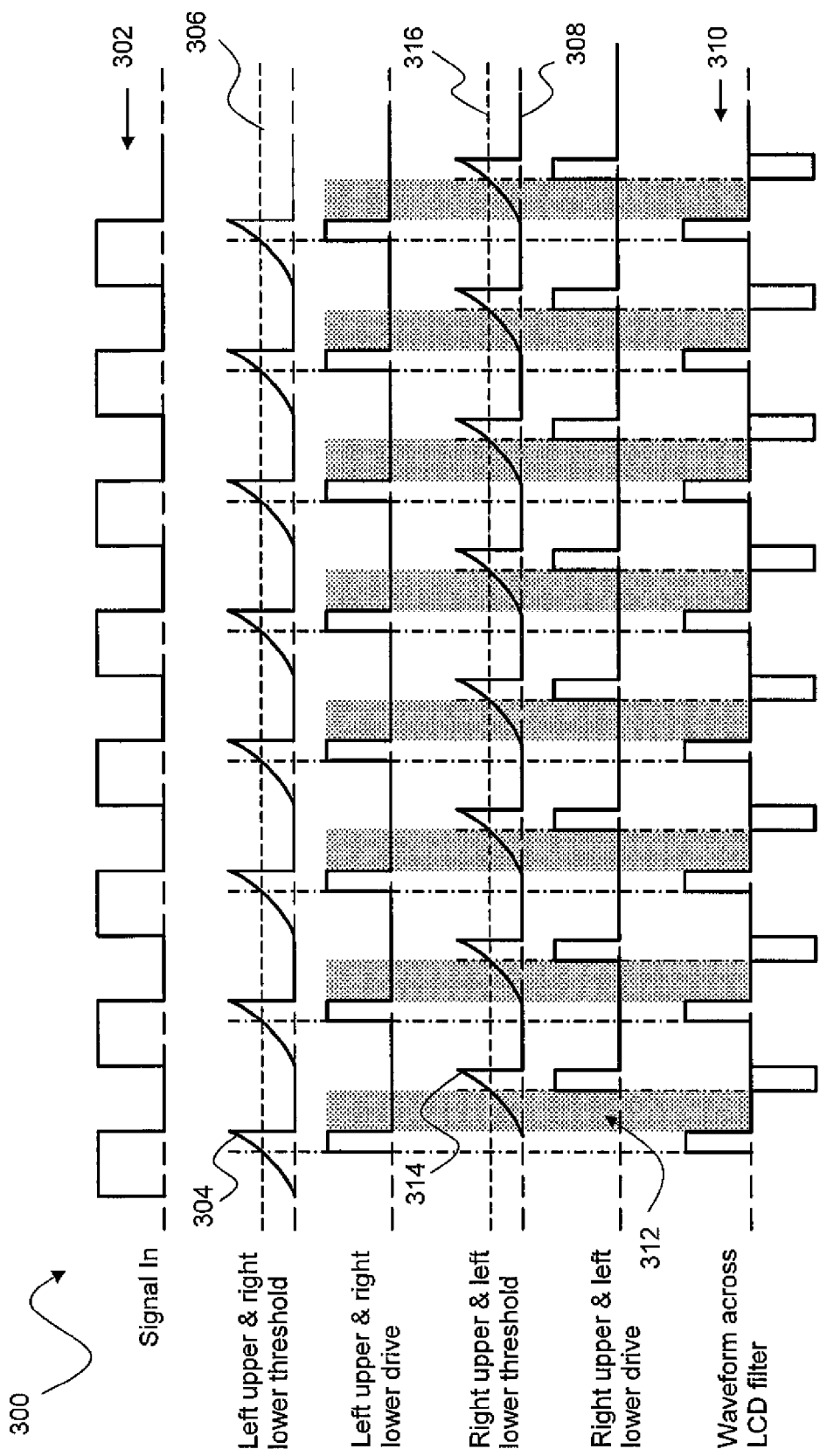
FIG. 3 is a group of waveforms illustrating voltage levels at various points of the circuit diagram of FIG. 2 useful in understanding the operation of the circuit.

Referring to FIG. 2 and the waveforms diagram 300 of FIG. 3, when logic high is seen at the S1 Control from the signal on line 240 as illustrated in waveform 302, switches S1*a* and S1*b* connect one end of capacitors $C_1$ and $C_4$ through resistors $R_1$ and $R_4$ respectively to the On Voltage supply. This provides a charging voltage to capacitors $C_1$ and $C_4$ resulting in a ramp up 304 of the voltage to the left upper driver 204 and lower right drive 216. When this ramp up 304 voltage reaches threshold voltage 306 of the drivers, the drivers turn on.

Simultaneously, when this logic high is seen at the S2 control, switches S2*a* and S2*b* turn off. This causes the threshold voltages 226 and 234, respectively, of the left lower driver 206 and right upper drive 214 to switch to the off voltage substantially instantaneously, which causes the left lower and right upper drives to turn off immediately. The Off Voltage level is represented as Off Voltage 308 in FIG. 3. After a delay produced by the time delay function of resistor-capacitor series circuits $R_1C_1$ and $R_4C_4$, the left upper driver 204 and right lower drive 216 are turned on. The same off-delay-on operation occurs when the left upper driver 204 and right lower drive 216 turn off and the right upper driver 214 and left lower drive 206 turn on as a result of the time delay function of resistor-capacitor series circuits $R_3C_3$ and $R_2C_2$.

As a result of this operational sequence, a voltage waveform 310 is impressed across LCD filter 202. From an overall view of waveforms 300, it will be seen that when Signal In as seen at waveform 302 is applied to Signal In line 240, as the signal goes to a high logic level a ramp voltage 304 begins to be produced based on the RC time constants of timing circuits $R_1C_1$ and $R_4C_4$. When the ramp voltage reaches a threshold level 306, drivers 204 and 216 turn on. When the Signal In voltage on line 240 goes to a low logic level, drivers 204 and 216 substantially immediately turn off and another timing operation is conducted based on the time constants of timing circuits $R_2C_2$ and $R_3C_3$. This time period is represented in the shaded area 312. When the ramp voltage 314 for these timing circuits reach a threshold level 316, drivers 206 and 214 turn on until the Signal In line 240 again goes to a logic high level where drivers 206 and 214 substantially immediately turn off and the cycle repeats itself so long as Signal In on line 240 continues to repeat.

Those of ordinary skill in the art will appreciate that while the present disclosure has illustrated the use of RC timing circuits to provide switching delay for the driver circuits, other types of delay producing circuitry may be employed including, without limitation, digital circuitry.

In this manner, the waveform applied to LCD filter 202 alternates such that there is no period during which either the left drivers 204, 206 or the right drivers 214, 216 are simultaneously on so as to avoid shunting of the Shade Voltage supply to ground. Such operation avoids the previously encountered electrical component stress and high battery drain.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. An automatic darkening filter eye protection device, comprising:
   a liquid crystal device filter having a first control terminal and second control terminal;
   first and second driver circuits coupled to said first control terminal, each said first and second driver having a respective control input;
   third and fourth driver circuits coupled to said second control terminal, each said third and fourth driver circuits having a respective control input;
   first, second, third, and fourth time delay circuits coupled respectively to said control input of said first, second, third, and fourth driver circuits;
   first, second, third, and fourth switches coupled respectively to said first, second, third, and fourth time delay circuits, each said first, second, third, and fourth switch configured to couple its respective time delay circuit to one of an on voltage supply or an off voltage supply; and
   a switch control circuit configured to alternately operate said first and fourth switches concurrently and said second and third switches concurrently.

2. A device as in claim 1, wherein said first, second, third, and fourth time delay circuits each comprise a resistor and a capacitor.

3. A device as in claim 1, wherein said first and third driver circuits are configured to couple a shade voltage supply to said first and second control terminal respectively of said liquid crystal device filter.

4. A device as in claim 1, wherein said second and fourth driver circuits are configured to couple said first and second control terminal respectively of said liquid crystal device filter to ground potential.

5. A device as in claim 1, wherein each of said first, second, third, and fourth driver circuits includes a threshold circuit establishing a driver turn on voltage level.

6. A method for operating an automatic darkening filter eye protection device, comprising:
   alternately reversing polarity of a voltage supply applied to a pair of control terminals of a liquid crystal device (LCD) filter between a first polarity and a second polarity; and
   delaying application of the voltage at the first polarity for a predetermined time following removal of the voltage at the second polarity and ramp up of the first polarity voltage to a threshold voltage.

7. The method of claim 6, further comprising:
   delaying application of the voltage at the second polarity for a predetermined time following removal of the voltage at the first polarity and ramp up of the second polarity voltage to a threshold voltage.

8. A method for operating an automatic darkening filter eye protection device, comprising:
   alternately reversing polarity of a voltage supply applied to a pair of control terminals between a first polarity and a second polarity; and
   delaying application of the first polarity for a predetermined time following removal of the second polarity; and
   wherein the predetermined time is determined based on the time required to charge a capacitor through a resistor to a predetermined voltage level.

9. The method of claim 6, further comprising:
   applying a reference potential to the pair of control terminals during the predetermined time.

* * * * *